US010925325B2

(12) United States Patent
Norton

(10) Patent No.: US 10,925,325 B2
(45) Date of Patent: Feb. 23, 2021

(54) INFANT GARMENT ADAPTED FOR DIAPER CONDITION INSPECTION

(71) Applicant: Michelle Norton, Bend, OR (US)

(72) Inventor: Michelle Norton, Bend, OR (US)

( * ) Notice: Subject to any disclaimer, the term of this patent is extended or adjusted under 35 U.S.C. 154(b) by 27 days.

(21) Appl. No.: 16/208,380

(22) Filed: Dec. 3, 2018

(65) Prior Publication Data
US 2019/0289923 A1    Sep. 26, 2019

Related U.S. Application Data

(60) Provisional application No. 62/617,791, filed on Mar. 22, 2018.

(51) Int. Cl.
*A41B 13/04*    (2006.01)
*A41D 13/12*    (2006.01)
*A41D 1/06*    (2006.01)
*A61F 13/49*    (2006.01)

(52) U.S. Cl.
CPC .............. *A41B 13/04* (2013.01); *A41D 1/062* (2013.01); *A41D 13/1272* (2013.01); *A41B 2300/30* (2013.01); *A61F 13/49* (2013.01)

(58) Field of Classification Search
CPC ........... A41B 13/04; A41B 13/08; A41B 9/08; A41B 9/005; A41B 9/007; A41B 9/02; A41B 9/026; A41B 13/005; A41B 2300/30; A41B 2300/32; A41B 2300/324; A41B 2300/326; A41B 2300/33; A41B 9/001; A41B 9/04; A41D 1/06; A41D 1/062; A41D 1/065; A41D 1/067; A41D 1/08; A41D 11/00; A41D 13/1272; A41D 13/1254; A41D 27/28; A41D 13/02; A41D 27/08; A41D 10/00; A41D 13/1236
USPC ......... 2/80, 111, 78.2, 78.4, 75, 79, 83, 408, 2/227, 228, 238, 244, 243.1, 279, 919, 2/112, DIG. 1
See application file for complete search history.

(56) References Cited

U.S. PATENT DOCUMENTS

| | | | | | |
|---|---|---|---|---|---|
| 1,168,023 | A | * | 1/1916 | Morley | A41B 9/08 2/78.2 |
| 2,018,120 | A | * | 10/1935 | Bumbarger | A41B 9/08 2/78.2 |
| 2,149,416 | A | * | 3/1939 | Blankenhorn | A41B 9/08 2/78.2 |
| 2,812,516 | A | * | 11/1957 | Hoffman | A41B 13/04 2/80 |
| 3,279,469 | A | * | 10/1966 | Schustack | A41C 1/003 450/113 |
| 4,446,575 | A | * | 5/1984 | Davis | A41D 13/1254 2/400 |

(Continued)

FOREIGN PATENT DOCUMENTS

| | | | | |
|---|---|---|---|---|
| GB | 456497 A | * | 11/1936 | ............... A41B 9/08 |
| WO | WO-03059100 A1 | * | 7/2003 | ......... A41D 13/1254 |

*Primary Examiner* — Jameson D Collier
(74) *Attorney, Agent, or Firm* — Donn K. Harms

(57) ABSTRACT

A garment adapted for wearing by a diaper wearer which surrounds a diaper and provides at least one inspection aperture forming an opening through the garment employable for visual, olfactory, or tactile inspection of the underlying diaper without removal of the garment. One or a plurality of the inspection apertures may be provided in inspection positions adapted to locate them aligned with or adjacent the perimeter edge of the underlying diaper.

8 Claims, 3 Drawing Sheets

(56) References Cited

U.S. PATENT DOCUMENTS

| | | | | |
|---|---|---|---|---|
| 4,533,355 A * | 8/1985 | Fair | A61F 5/445 | 2/238 |
| 4,637,078 A * | 1/1987 | Southwell | A41B 9/007 | 2/408 |
| 4,930,161 A * | 6/1990 | Cohen | A41D 13/1254 | 2/114 |
| 5,210,879 A * | 5/1993 | Miller | A41D 13/012 | 2/227 |
| 5,341,515 A * | 8/1994 | Cohen | A41D 13/1254 | 2/227 |
| 6,092,240 A * | 7/2000 | Weller | A41D 13/1254 | 2/114 |
| 6,163,883 A * | 12/2000 | Hong | A41D 27/28 | 2/69 |
| 6,324,699 B1 * | 12/2001 | Cosmah | A41B 11/14 | 2/239 |
| 7,530,118 B2 * | 5/2009 | Osborne | A41B 13/06 | 2/111 |
| 7,770,237 B1 * | 8/2010 | Wright | A41D 13/1272 | 2/111 |
| 8,359,663 B2 * | 1/2013 | Blomkwist | A41B 13/08 | 2/111 |
| 8,479,320 B2 * | 7/2013 | Swafford | A41D 1/00 | 2/227 |
| 8,914,912 B2 * | 12/2014 | Stevenson | A41D 13/012 | 2/82 |
| 2006/0277649 A1 * | 12/2006 | Smith | A41B 11/006 | 2/69 |
| 2009/0320184 A1 * | 12/2009 | Schaefer | A41B 9/02 | 2/405 |
| 2013/0104294 A1 * | 5/2013 | Edwards | A41B 9/04 | 2/408 |
| 2014/0053314 A1 * | 2/2014 | Blomberg | A41B 13/08 | 2/80 |
| 2014/0123363 A1 * | 5/2014 | Templeton | A41B 13/08 | 2/69 |
| 2014/0317828 A1 * | 10/2014 | Holsinger | A41B 13/08 | 2/80 |
| 2017/0119066 A1 * | 5/2017 | Robinson | A61F 13/74 | |
| 2017/0303601 A1 * | 10/2017 | Lopina DeMaria | A41B 13/08 | |
| 2017/0303605 A1 * | 10/2017 | Barasa | A41D 27/285 | |

* cited by examiner

INFANT GARMENT ADAPTED FOR DIAPER CONDITION INSPECTION

BACKGROUND OF THE INVENTION

1. Field of the Invention

The present invention relates to a device for infants configured for diaper inspection. More particularly the invention relates to an infant garment or configuration thereof which includes one or a plurality of accessible apertures positioned to allow visual or olfactory inspection of the underlying diaper without need for removal of the garment worn by the infant and covering the diaper.

2. Prior Art

Newborn children and infants up to the time they are toilet-trained, conventionally are clothed in diapers which are adapted to substantially contain the liquid or solid material soiling the diaper. In the case of liquid such as urine, modern disposable diapers employ materials to absorb the liquid in a gel. However, in the case of solid waste it is the seal of the perimeter edges of the diaper that provide the means to maintain such waste within the confines of the diaper.

One issue which the parents of infants are constantly battling is that of diaper rash. Diaper rash is a skin irritation which is well known to be an uncomfortable, if not painful, condition suffered by infants. It is generally caused by a soiled diaper which maintains the liquid or solid material adjacent the skin of the infant. The longer the duration of such contact of a soiled diaper with the skin of the infant, the more the potential for development of diaper rash on the skin of the infant. While medications may be employed to battle and help cure the scourge of diaper rash, an infant will continue to endure the discomfort of it until cured. Such a cure is of course aggravated and delayed by continued contact of the skin suffering the rash, with soiled diapers.

To that end, parents and caretakers of infants and children wearing diapers attempt to be ever vigilant in determining if the child has soiled their diaper. Should such be determined, a removal and replacement of the diaper and a cleaning of the contacted skin areas of the infant or child, is immediately provided.

However, when the infant or child is wearing pants or a one-piece garment of pants and shirt over the underlying diaper, engaged about the bottom of the child, ascertaining if the diaper is soiled becomes problematic. Because most diapers absorb a good deal of wetness, such is not easily detected without removing the clothing covering the diaper in a time consuming and frequently child-irritating maneuver. With regard to solid soiling of the diaper, a sniff-test or olfactory determination is sometimes attempted by the parent prior to removing the overlying clothing to inspect the diaper.

In the inspection for both liquid or solid soiling, after the time consuming and child irritating removal of clothing to inspect the contents of the diaper, frequently the parent finds such action was a waste of time and the child simply had gas, or has not soiled the diaper at all. This requires reinstating the connections on the diaper to seal it about the perimeter and repositioning of the removed clothing over the diaper and on the child. Unfortunately, within a short time, a reinspection must again be initiated to the irritation of both the parent and child.

The infant clothing device and method of configuring such herein, provides a solution to the ongoing false alarms and wasted effort involved in diapering an infant or child. The clothing device configured either as separate pants, or as a one-piece garment of pants and a top, is provided with one or a plurality of inspection apertures located preferably on the rear portion of the pants.

These inspection apertures have openings which are narrow and elongated and have an axis which follows a substantially angled pathway relative to the axis of the pants running between the crotch and waist centered between both legs portions. The underlying diaper and edge thereof can be physically inspected by reaching through the opening of the aperture to feel the interior of the diaper, or by sniffing the diaper through the aperture where it crosses over the perimeter edge of the diaper, which may be lifted during this process to provide a much more accurate discerning as to whether the underlying diaper has been soiled.

The forgoing examples of related art as to diaper inspection and clothing covering such, and limitations related therewith, are intended to be illustrative and not exclusive, and they do not imply any limitations on the invention described and claimed herein. Various limitations of the related art will become apparent to those skilled in the art upon a reading and understanding of the specification below and the accompanying drawings.

SUMMARY OF THE INVENTION

The diaper covering clothing device herein disclosed and described achieves the above-mentioned goals through the provision of diaper covering clothing having one or a plurality of openings or inspection apertures formed in the pants or pants portion of a once-piece configuration of such diaper covering clothing. The inspection aperture or plurality thereof are preferably positioned in the section of material of the pants portion of the garment that contacts the backside of the infant so as to position them away from the prying hands of older infants who are still wearing diapers. Further, in the case of solid waste soiling of the underlying diaper and rear end, positioning allows for more accurate olfactory sensing or sniffing to determine the presence of solid waste in the underlying diaper without the need to remove the clothing.

The inspection apertures are preferably elongated and formed as an elongated slit or narrow oval shaped opening communicating through the fabric forming the diaper covering garment. While originally rectangular or round holes were employed to provide a wide view and opening, during testing it was found unexpectedly, that forming the openings as elongated slits or narrow-diameter ovals is a superior configuration. This was found because slits may be formed larger than large rectangles and ovals without weakening the fabric. Further, the likelihood a portion of the elongated slit inspection opening would cross over a perimeter edge of the diaper, which vary in size by brand, is significantly increased.

By positioning the opening of the aperture in an inspection position adapted to cross over or run adjacent to the perimeter edge of the underlying diaper, the opening also defines an inspection area adapted for visual inspection for leaking from the perimeter edge, and for tactile inspection by placing a finger through the opening and under the diaper to raise it for more accurate touch, and an olfactory inspection port. Thus, the opening defines a visual, olfactory, and tactile inspection port where the user may view, sniff, or touch the underlying diaper.

Still further, forming the elongated slit or narrow oval shaped inspection aperture, with an axis following a diagonal angle relative to the axis running through the center of the pants portion or garment, was found to further increase the likelihood that a portion of the perimeter edge of the underlying diaper, would be visible through or immediately adjacent to the formed opening, as well as accessible therethrough. As such, while the elongated slit or oval-shaped inspection aperture can be formed substantially parallel to the seam defining the axis of the garment, positioning it in an inspection position running at substantially an angle of 10-80 degrees relative to the center seam of the garment or a line running from the crotch to the waist, is preferred. This is because such an angled axis and positioning increases the likelihood of an intersection with some portion of the perimeter edge of the underlying diaper.

Additionally found during experimentation was that the addition of a member, preferably a flexible member extending from an engagement adjacent one side of the elongated slit, provided additional enhancements to the function of the device herein. Because it is preferred to employ a moveable flap over the formed inspection aperture for aesthetic as well as functional reasons, and because forming the flap of the same fabric pattern as the pants portion is more aesthetic, once the flap was closed it made it hard to discern the location of the inspection openings.

Inclusion of a member engaged at one end to either one half of the releasable fastener used to hold the distal end of the flap engaged, or to the garment adjacent the opening, provided a visual target to users as to the position of the inspection aperture underneath the secured flap. During experimentation it was found that holding the member while disengaging the distal end of the flap, made it easier to do so, while concurrently preventing tearing of the fabric where the fasteners became hard to disengage.

Further, once the flap was disengaged, the elongated member can be pulled to thereby widen the narrow slit or oval opening and provide a better view of the underlying perimeter edge of the diaper thereby allowing the user to better inspect visually and by sniffing without having to physically touch the diaper. Consequently the member, preferably with a loop at the distal end, is preferred, and preferably in a flexible configuration so it bends when sat upon.

With respect to the above description, before explaining at least one preferred embodiment of the herein disclosed diaper covering clothing device and method in detail, it is to be understood that the invention is not limited in its application to the details of construction and to the arrangement of the components in the following description or as illustrated in the drawings. The diaper covering clothing invention herein described is capable of other embodiments and of being practiced and carried out in various ways which will be obvious to those skilled in the art. Also, it is to be understood that the phraseology and terminology employed herein are for the purpose of description and should not be regarded as limiting.

As such, those skilled in the art will appreciate that the conception upon which this disclosure is based, may readily be utilized as a basis for designing of clothing worn over diapers allowing for inspection thereof without removal, and methods and systems for carrying out the several purposes of the present disclosed clothing device. It is important, therefore, that the claims be regarded as including such equivalent construction and methodology insofar as they do not depart from the spirit and scope of the present invention.

It is an object of the invention to provide clothing configured to be in a worn position over diapers of a diaper wearer which provides an inspection port for visual, olfactory, or tactile inspection of the underlying diaper without removal of the clothing.

It is another object of the invention to provide such a clothing device which provides one or a plurality of inspection apertures having elongated narrow openings in angled positionings across an inspection area of the pants portion of the garment.

It is a further object of the invention to provide such a diaper covering clothing device having inspection apertures which are removably covered with flaps and which may include an elongated member, engaged adjacent one side of the aperture to provide a visual target to open the flap as well as a means to enlarge the view or air passage through the opening by a pulling thereon.

Further objects of the invention will be brought out in the following part of the specification, wherein detailed description is provided for the purpose of fully disclosing the invention but without placing limitations thereon.

BRIEF DESCRIPTION OF DRAWING FIGURES

DETAILED DESCRIPTION OF THE PREFERRED EMBODIMENTS OF THE INVENTION

Figure 1:
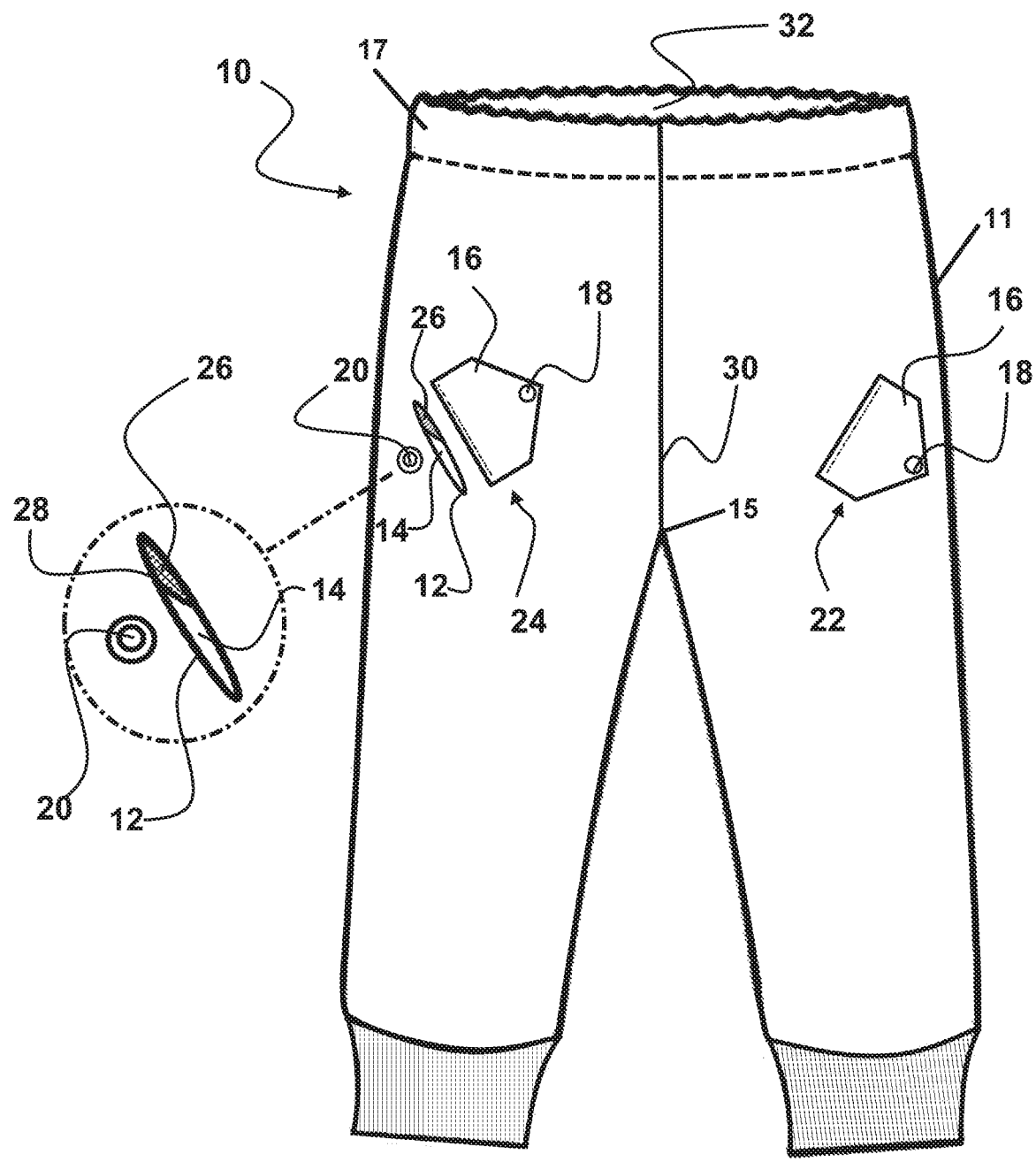
FIG. 1 depicts the device herein showing a plurality of inspection apertures communicating through an inspection area of the fabric of the pants portion of a diaper-covering garment where one such inspection opening is covered by a flap and another inspection aperture is viewable.

Now referring to drawings in FIGS. 1-4, wherein similar components are identified by like reference numerals, there is seen in FIG. 1 the device 10 showing the body of a diaper-covering garment 11 having at least one, and preferably a plurality of elongated inspection apertures 12 formed by slits herein referred to as openings 14, communicating through the fabric forming the diaper covering garment 11 at respective inspection positions. While shown as pants in FIGS. 1-2 and a combined garment 11 in FIG. 4, the garment 11 can be any diaper covering garment 11 such as shorts or other garments, which adapted for wearing in a worn position on the body of user in a position covering and surrounding a diaper worn by the wearer.

As shown, the inspection apertures 12 are elongated and formed of openings 14 configured preferably as a narrow slit, as shown. A slit configuration maintains little or no gap between the sides of the opening 14, such as an elongated oval or rectangular opening 14 which may have a length preferably from one to six inches. The perimeter edge of the openings 14, shown in the enlarged portion of FIG. 1 in dark line, may be reinforced such as with an overlock stitch of thread or yarn or elastic, or other means to reinforce and urge and maintain the opening 14, with both sides of the opening 14 adjacent each other, or to maintain them just slightly spaced from each other. Such a spacing is preferred to be less than one inch and preferably less than one half inch for the aesthetics of the garment and functionally to help avoid leakage therethrough.

At least one opening 14 of one aperture 12 is so positioned at an inspection position in an inspection area 19 of the garment 11. The aperture 12, having an opening 14 in this inspection position, is positioned in the garment 11 to be located adjacent to, or cross over, a lower perimeter edge 28 of a diaper 26 on a person such as an infant or toddler. uch an inspection position in an inspection area 19 of the garment 11, in experimentation, has been found to be a placement where the center area of the opening 14 of the aperture 12, is located between the waist 17 of the garment and the crotch 15, and a distance of one to ten inches above the centrally located crotch 15 area of the garment 11, and situated to the left or right thereof.

An inspection position of the opening 14 in the inspection area 19 which positions the central area of the opening 14 of the aperture 12 one to six inches above the crotch 15 and below the waist 17 area, for most children and infants, has been found to work particularly well. Such is shown for example in FIG. 3. In any case, by inspection area 19 of the garment 11 is meant substantially an area of the garment 11 located between the crotch 15 and a waist 17 area thereof where the opening 14 may be located at the inspection position. Those skilled in the art will realize the inspection position of the openings 14 may vary but can be determined with each garment 11 especially were as noted herein, the axis of the opening angles relative to the seam or a line noted, such that the opening 14 is running across the lower perimeter edge 28 of a diaper worn by the wearer of the garment 11 and thereafter reproduced in a size of garment 11 where such location positions are substantially so positioned on a wearer. All such location positions are intended to be within the scope of this patent.

The crotch 15 area of the garment 11 such as on pants or shorts or what is known as a "onesie," is a center area positioned between the legs of the diaper wearer. If the opening 14 were positioned at that point, it would run substantially perpendicular to the waist 17 vertically, and with the garment 11 being worn, would generally be substantially aligned with the spine of the wearer. The aperture 12 with the opening 12 is better placed to the left or right of the crotch 15 and the imaginary line running perpendicular to the waist 17, because such positions the opening 14 with easier access when the wearer is sitting or lying on one side. Also, it has been found as noted herein, that running the axis of the elongated narrow opening 14 of the aperture 12, along an angle relative to the seam running perpendicular from the crotch 15 of the garment 11 to the waist 17, or, if no seam exists, then along an angle relative to an imaginary line running from the crotch 15 to the waist 17, works best to place some portion of the opening 14 running across the lower perimeter 28 edge of the diaper 26, or immediately adjacent thereto.

Also shown are an optional but preferred flap 16 which is engaged to the fabric forming the garment 11 on a first end adjacent a first side of the inspection apertures 12, and folds over and covers the aperture 12. The flap 16 may be so engaged by sewing or adhesive or other permanent means for engaging the first side of the flap 16 to the fabric of the garment 11 of the device 10. While the device 10 can be formed with simply the inspection apertures 12 formed as slits with sides substantially adjacent, the flap 16 is preferred for aesthetics and in case of leakage which might traverse through the opening 14 of the apertures 12.

While the device 10 will work with just a flap 16 covering the inspection apertures 12, on an opposite second side of the flap 16 is preferably positioned a first releasable fastener 18 which is removably engageable with a second releasable fastener 20 engaged adjacent an a second side of the inspection aperture 12 opposite the first side of the inspection aperture 12. The first releasable fastener 18 and second releasable fasteners 20 are essentially two halves of a disengageable fastener such as a button, a snap, hook and loop fabric, magnets, or other releasable fasteners as would occur to those skilled in the art.

When the first releasable fastener 18 is engaged with the second releasable fastener 20 it holds the flap 16 in a covering position 22 where it covers the underlying opening 14 of the inspection aperture 12. When the fabric forming the flap 16 has the same pattern as that of the garment device 10, it blends into the surrounding fabric visually.

The flap 16 is moveable to an open position 24 by separating the first releasable fastener 18 from the second releasable fastener 20 and rotating or folding it in a direction away from the inspection aperture 12 thereby exposing the opening 14 and a portion of the diaper 26 such as preferably the lower perimeter edge 28 of the diaper 26 within the opening 14. With the flap 16 in the open position 24, the user may visually inspect the diaper 26 and perimeter edge 28 thereof for leakage. Further, the opening 14 in the inspection position in all modes, defines an inspection port. Through this defined inspection port for visual, olfactory, or tactile inspection of the underlying diaper without removal of the clothing. This is provided because the user may easily sniff the air through the opening to discern if any odor is present indicative of solid or liquid soiling of the diaper 26, or may touch the diaper through the opening 14 for a tactile inspection, or may view the diaper through the opening 14 to visually inspect it.

Further, if desired, the user may insert a finger through the opening 14 and under the exposed perimeter edge 28 of the diaper 26 to feel for moisture or the like. Once the user is finished using the defined inspection port, the flap 16 may be repositioned to the covering position 22 and the first releasable fasteners 18 engaged to the second releasable fastener 20 to hold the flap 16 in the covering position 22.

As shown in all the drawings, the elongated opening 14 of the inspection apertures 12 is preferably maintained narrow and while it may run parallel to the pants portion 32 axis defined by the seam 30 of the pants portion of the garment 11, preferably the axis of the opening 12 of the elongated inspection aperture 14, runs at an angle thereto such as between 10-80 degrees. Experimentation has shown an angle between 20-60 degrees relative to the axis defined by the seam 30, or an imaginary straight line centered on the garment 11 and running between the crotch 15 and the waist 17, works well to position some portion of the opening 14 in an inspection position which is located over or adjacent to the perimeter edge 28 of the underlying diaper 26. Elongating the slit or narrow opening 14 of the aperture 12 to a length between 2-6 inches is also preferred to also insure that some portion thereof is aligned over the perimeter edge 28 or immediately adjacent a diaper 26.

Figures 2, 3:
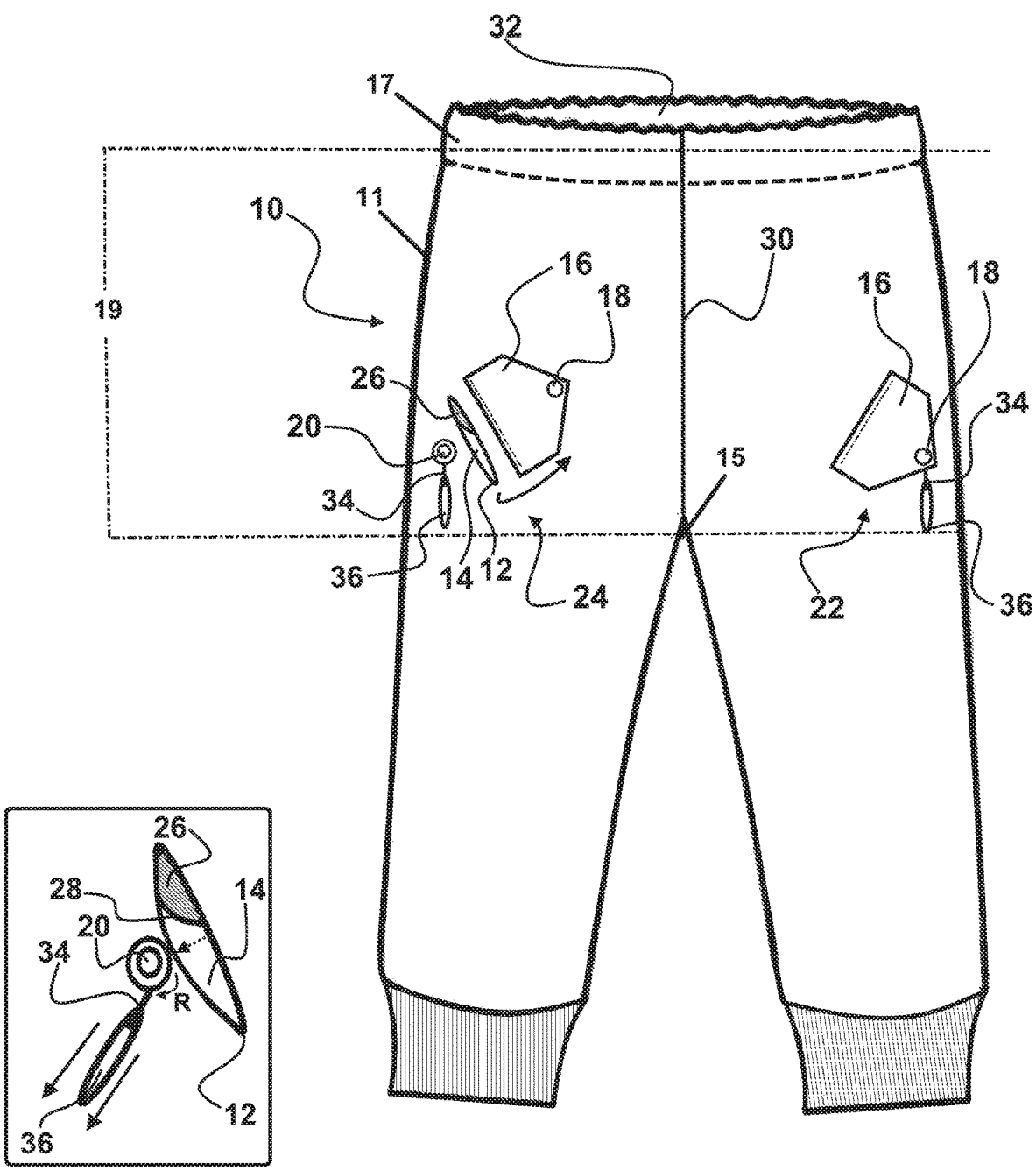
FIG. 2 shows a view similar to that of FIG. 1 showing the pants portion of the diaper covering garment herein and depicting openings at inspection positions in an inspection area along with members engaged at a first end adjacent the opposite side of the openings from the engagement of the first side of the flap.
FIG. 3 depicts an enlarged view of the inspection aperture located at an inspection position and showing the increase in opening size achieved by pulling upon the elongated member which may rotate.

In FIG. 2 is depicted the garment device 10 herein, showing a preferred mode similar to that of FIG. 1. As shown, the pants portion 32 of the diaper covering garment 11 of the device 10 has at least one, and as shown, a plurality of elongated inspection apertures 12. The openings 14 of the narrowly defined openings 14 therein run on an axis at the above noted angle relative to the seam 30 defining an axis of the pants portion 32. The flap 16 which is preferably included, is positionable between the open position 24 and a covering position 22, by disengagement of the separable first releasable fastener 18 from the second releasable fastener 20.

In FIG. 2 is also shown a particularly preferred member 34 which is preferably formed of flexible material such as fabric or polymeric material or chord or the like. This member may be rigid however forming it flexible makes it more comfortable if sat upon. The member 34 extends from a first end engaged to the material of the garment 11, adjacent a side of the inspection aperture 12 opposite the side on which the first end of the flap 16 is engaged. By adjacent is meant at the edge of the opening 14 of the aperture 14 or within four inches thereof. This positioning of flap engagement and the engagement of the first end of the member 34 on opposite sides of the inspection aperture 12 is particularly preferred. This is because such positioning allows the user to pull on the distal end of the flap 16 adjacent the first releasable fastener 18 in one direction, and the distal end of the member 34 in an opposite direction, and thereby enlarge a diameter of the opening 14 temporarily such as shown in FIG. 3. Also shown in FIG. 2, the members 34 also provide a visual beacon or target to the user to identify the location of the inspection apertures 12 when the flap 16 is in the covering position 22 and formed in the same pattern or fabric of the garment 11 which tends to hide it in plain sight. Still further, the member 34 allows a user to pull the narrow gap of the opening 14 of the aperture 12 and make it wider as needed.

As shown in FIG. 3, additionally preferred in the garment 11 of the device 10 is the provision of such members 34 having a loop 36 at the distal end thereof. This loop 36 provides the user an easy means to engage a finger therein to impart force in a direction away from the flap 16 as noted above to increase the diameter of the opening 14 of the inspection aperture 12. However, the distal end of the member 34 may also formed without the loop 36 and pinched during use to pull the opening 14 wider if desired.

Further shown in FIG. 3 is the member 34 rotationally engaged at a first end thereof, at or adjacent the fastener 20. Where a snap or similar fastener 20 is employed, it can rotate in-between the fastener 20 and the material forming the garment 11. This rotational engagement shown as R.

A rotational engagement R, while optional, has been found in experimentation to work better in tight surroundings, and has been found to allow the user to also pull in any direction should pulling in one direction not provide the view or access they need to determine. The rotation of the member 34 is helpful where the infant has managed to position the garment 11 askew of the underlying diaper so as to allow the user to rotate the member 34 in a direction to better situate the aperture 14 for inspection.

Figure 4:
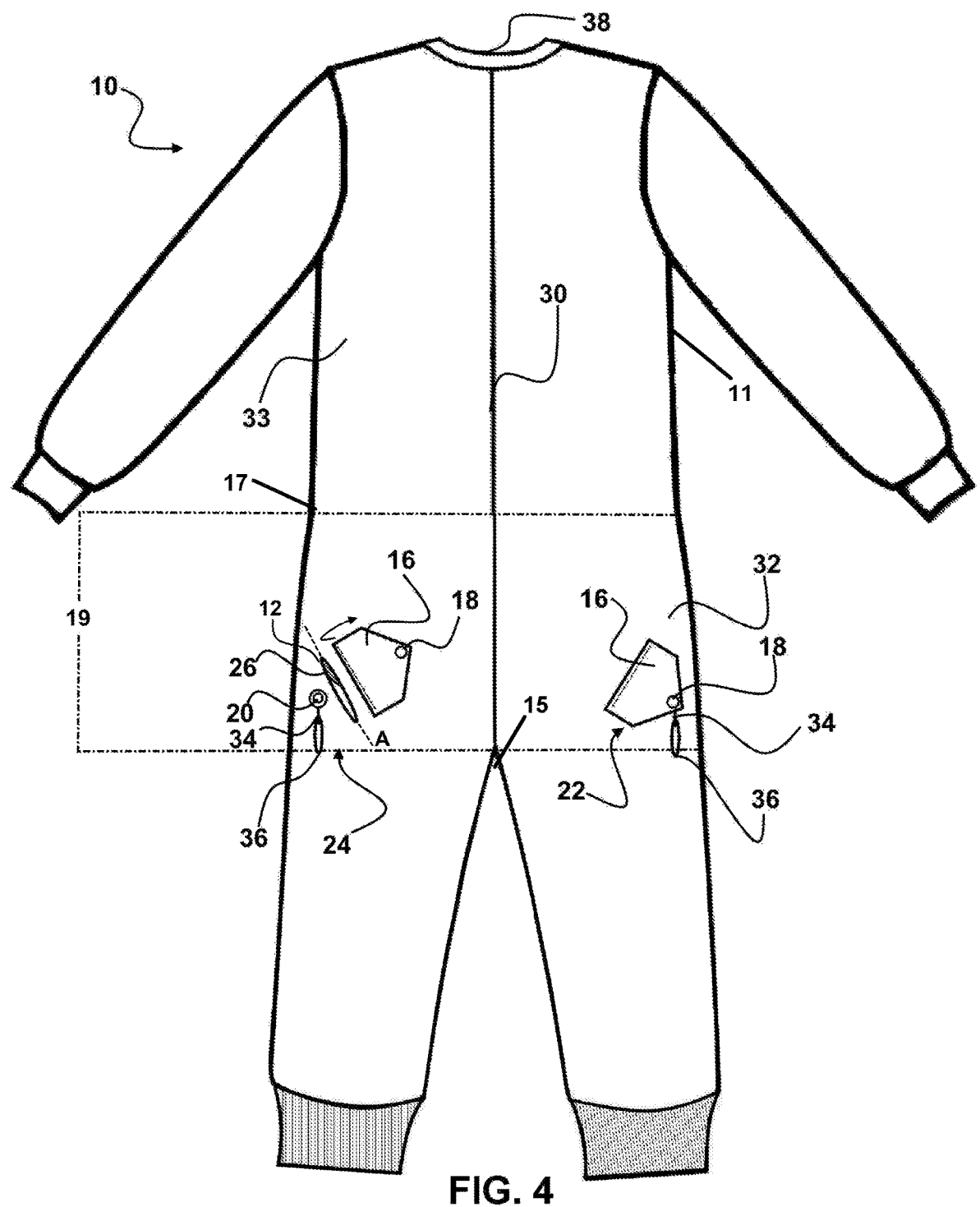
FIG. 4 shows a one-piece mode of the diaper covering garment device herein, showing a plurality of inspection apertures at inspection positions having openings formed into the inspection area of a pants portion of the garment each with preferably flexible members engaged at respective first ends adjacent one side of the elongated openings of the inspection apertures.

In FIG. 4 is shown a one-piece mode of the diaper covering garment 11 herein commonly known as a "onesie," having a pants portion 32 and a shirt portion 33 engaged thereto. As can be seen, at least one, and preferably a plurality of inspection apertures 12 are included having openings 14 positioned to a distance above the crotch 15 to overlap a perimeter edge 28 portion of the underlying diaper 26. This mode as with those above, is employable preferably with the members 34 engaged on the opposite side of the opening 14 from the engagement of the first end of the flap 16. This type of engagement and positioning allows the user an easy manner to pull on the member 34 and flap 16 concurrently, and temporarily increase the size of the diameter or distance between opposing side edges of the opening 14 of the inspection aperture.

As with the mode of the device 10 having only a pants portion 32 forming the garment 11, the elongated narrow openings 14 of the inspection apertures 12 run at an angle relative to the axis of the garment 11 defined by the center seam 30 or an imaginary line running between the crotch 15 at the intersection of the leg portions at a lower end, to the center of the waist 17 area or the center of the neck opening 38 of the garment 11 of the device 10.

While all of the fundamental characteristics and features of the garment device 10 having inspection apertures 12 for inspecting the condition of an underlying diaper 26 have been shown and described herein, with reference to particular embodiments thereof, a latitude of modification, various changes and substitutions are intended in the foregoing disclosure and it will be apparent that in some instances, some features of the invention may be employed without a corresponding use of other features without departing from the scope of the invention as set forth. It should also be understood that various substitutions, modifications, and variations may be made by those skilled in the art without departing from the spirit or scope of the invention. Consequently, all such modifications and variations and substitutions are included within the scope of the invention as defined by the following claims.

What is claimed:

1. A garment adapted for wearing by a diaper wearer in a worn position which surrounds a diaper worn by said diaper wearer, said garment comprising:
   a garment body having a crotch and a waist, said garment body having an inspection area positioned between said crotch and said waist of said garment body;
   a vertical centerline of said garment running between said crotch and said waist, said vertical centerline defining a right half and a left half of said garment;
   an inspection aperture formed entirely within said inspection area of said garment body, said inspection aperture positioned entirely within said left half or entirely within said right half of said garment;
   said inspection aperture being an opening, the opening having a central area positioned at an inspection position within said inspection area of the garment body;
   said opening at said inspection position locating an inspection portion of said opening adjacent to a perimeter edge of said diaper with said garment in said worn position;
   said opening having a first side edge opposite a second side edge;
   an elongated member having a first end and a distal end, said distal end of said elongated member located opposite to said first end of said elongated member;
   said first end of said elongated member directly secured to said inspection area of said garment body adjacent said second side edge, wherein said first side edge is across said opening from said first end of said elongated member;
   said distal end of said elongated member being free floating;

a flap having a first end secured to said inspection area of said garment body adjacent said first side edge of said opening;

said flap having a distal end being located opposite to said flap first end;

a fastener affixed to said inspection area of said garment body adjacent said second side edge of said opening; and said flap moveable between an engaged position held such that the flap covers said opening by an engagement of said distal end of said flap to said fastener, and an open position exposing said opening;

said opening being enlargeable by pulling said elongated member in a first direction, said first direction being in a direction away from said first side edge; and said opening defining an inspection port for visual, olfactory, or tactile inspection of the diaper without removal of the garment.

2. The garment of claim 1, additionally comprising:

said opening being elongated;

a spacing between said first side edge and said second side edge of said opening being less than one inch when said inspection area of said garment body is in a relaxed configuration.

3. The garment of claim 2, additionally comprising:

said elongated opening having a longitudinal axis, said axis running at an angle to said vertical centerline; and said angle being between 10-80 degrees.

4. The garment of claim 3, additionally comprising:

said angle is between 20-60 degrees; and said inspection position of the central area of the opening being located 1-6 inches above the crotch and being located below the waist.

5. The garment of claim 2, additionally comprising:

said elongated member having a loop.

6. The garment of claim 1, additionally comprising:

said first end of said elongated member secured to said fastener.

7. The garment of claim 6, additionally comprising:

said elongated member having a loop.

8. The garment of claim 1, additionally comprising:

said elongated member having a loop.

* * * * *